US00PP24896P2

(12) United States Plant Patent
Jones et al.

(10) Patent No.: US PP24,896 P2
(45) Date of Patent: Sep. 16, 2014

(54) ***DIASCIA* PLANT NAMED 'SUNJODIROPI'**

(50) Latin Name: *Diascia hybrida*
Varietal Denomination: Sunjodiropi

(71) Applicants: Jimmy Jones, St. Brides Netherwent (GB); David Jones, St. Brides Netherwent (GB)

(72) Inventors: Jimmy Jones, St. Brides Netherwent (GB); David Jones, St. Brides Netherwent (GB)

(73) Assignee: Suntory Flowers, Ltd., Tokyo (JP)

( * ) Notice: Subject to any disclaimer, the term of this patent is extended or adjusted under 35 U.S.C. 154(b) by 114 days.

(21) Appl. No.: 13/573,612

(22) Filed: Sep. 27, 2012

(51) Int. Cl.
*A01H 5/00* (2006.01)

(52) U.S. Cl.
USPC ..... Plt./425

(58) Field of Classification Search
USPC ..... Plt./425
See application file for complete search history.

*Primary Examiner* — Susan McCormick Ewoldt
(74) *Attorney, Agent, or Firm* — C. A. Whealy

(57) ABSTRACT

A new and distinct cultivar of *Diascia* plant named 'Sunjodiropi', characterized by its semi-upright and mounding plant habit; long and strong flowering stems; early and long flowering period; numerous large light dark rose pink-colored flowers; and good garden performance.

1 Drawing Sheet

Botanical designation: *Diascia hybrida.*
Cultivar denomination: 'SUNJODIROPI'.

BACKGROUND OF THE INVENTION

The present invention relates to a new and distinct cultivar of *Diascia* plant, botanically known as *Diascia hybrida*, and hereinafter referred to by the name 'Sunjodiropi'.

The new *Diascia* plant is a product of a planned breeding program conducted by the Inventors in St. Brides, Netherwent, Monmouthshire, United Kingdom. The objective of the breeding program is to create new *Diascia* plants with long and strong flowering stems and large attractive flowers.

The new *Diascia* plant originated from a cross-pollination conducted by the Inventors on Jun. 7, 2008 in St. Brides, Netherwent, Monmouthshire, United Kingdom with a proprietary selection of *Diascia hybrida* identified as code number d1001, not patented, as the female, or seed, parent and with a proprietary selection of *Diascia hybrida* identified as code number d76, not patented, as the male, or pollen, parent. The new *Diascia* plant was discovered and selected by the Inventors as a single flowering plant from within the progeny of the stated cross-pollination in a controlled greenhouse environment in St. Brides, Netherwent, Monmouthshire, United Kingdom on Aug. 20, 2008.

Asexual reproduction of the new *Diascia* plant by vegetative cuttings in a controlled greenhouse environment in St. Brides, Netherwent, Monmouthshire, United Kingdom since Aug. 20, 2008 has shown that the unique features of this new *Diascia* plant are stable and reproduced true to type in successive generations.

SUMMARY OF THE INVENTION

Plants of the new *Diascia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunjodiropi'. These characteristics in combination distinguish 'Sunjodiropi' as a new and distinct cultivar of *Diascia* plant:

1. Semi-upright and mounding plant habit.
2. Long and strong flowering stems.
3. Early and long flowering period.
4. Numerous large dark rose pink-colored flowers.
5. Good garden performance.

Plants of the new *Diascia* can be compared to plants of the female parent selection. Plants of the new *Diascia* differ primarily from plants of the female parent selection in the following characteristics:

1. Plants of the new *Diascia* have longer flowering stems than plants of the female parent selection.
2. Plants of the new *Diascia* have larger flowers than plants of the female parent selection.

Plants of the new *Diascia* can be compared to plants of the male parent selection. Plants of the new *Diascia* differ primarily from plants of the male parent selection in cold hardiness as plants of the new *Diascia* are more cold hardy than plants of the male parent selection.

Plants of the new *Diascia* can be compared to plants of the *Diascia barbarae* 'Diastu', disclosed in U.S. Plant Pat. No. 13,949. In side-by-side comparisons conducted in St. Brides, Netherwent, Monmouthshire, United Kingdom, plants of the new *Diascia* differed primarily from plants of 'Diastu' in the following characteristics:

1. Plants of the new *Diascia* were semi-upright whereas plants of 'Diastu' were outwardly spreading.
2. Plants of the new *Diascia* were larger than plants of 'Diastu'.
3. Plants of the new *Diascia* had thicker flowering stems than plants of 'Diastu'.
4. Plants of the new *Diascia* had longer leaves than plants of 'Diastu'.
5. Plants of the new *Diascia* and 'Diastu' differed in flower color.

6. Flower spurs of plants of the new *Diascia* were positioned towards the flower whereas flower spurs of plants of 'Diastu' were positioned away from the flower.

BRIEF DESCRIPTION OF THE PHOTOGRAPHS

The accompanying colored photographs illustrate the overall appearance of the new *Diascia* plant showing the colors as true as it is reasonably possible to obtain in colored reproductions of this type. Colors in the photographs may differ slightly from the color values cited in the detailed botanical description which accurately describe the colors of the new *Diascia* plant.

The photograph at the top of the sheet is a side perspective view of a typical flowering plant of 'Sunjodiropi' grown in a container.

The photograph at the bottom of the sheet is a close-up view of a typical inflorescence of 'Sunjodiropi'.

DETAILED BOTANICAL DESCRIPTION

The aforementioned photographs and following observations, measurements and values describe plants grown in 15-cm containers in an outdoor nursery in Higashiomi, Shiga, Japan and under cultural practices typical of commercial *Diascia* production. During the production of the plants, day temperatures averaged 23° C. and night temperatures averaged 13° C. Plants were four months old when the description was taken and five months old when the photographs were taken. In the following description, color references are made to The Royal Horticultural Society Colour Chart, 2007 Edition, except where general terms of ordinary dictionary significance are used.

Botanical classification: *Diascia hybrida* 'Sunjodiropi'.

Parentage:

*Female, or seed, parent*.—Proprietary selection of *Diascia hybrida* identified as code number d1001, not patented.

*Male or pollen parent*.—Proprietary selection of *Diascia hybrida* identified as code number d76, not patented.

Propagation:

*Type*.—By vegetative cuttings.

*Time to initiate roots, summer*.—About two weeks at 18° C.

*Time to initiate roots, winter*.—About 18 days at 18° C.

*Time to produce a rooted young plant, summer*.—About two weeks at 18° C.

*Time to produce a rooted young plant, winter*.—About 18 days at 18° C.

*Root description*.—Fibrous; white in color.

*Rooting habit*.—Freely branching.

Plant description:

*Plant form and growth habit*.—Semi-upright plant habit; vigorous growth habit; freely branching habit with numerous lateral branches developing per plant.

*Plant height*.—About 33.3 cm.

*Plant diameter* (*area of spread*).—About 37.5 cm.

Lateral branch description:

*Length*.—About 25 cm.

*Diameter*.—About 2.7 mm.

*Internode length*.—About 2.7 cm.

*Texture*.—Sparsely pubescent; longitudinally ridged.

*Color*.—Close to 144A tinted with close to 59A.

Foliage description:

*Arrangement*.—Opposite, simple.

*Length*.—About 2.9 cm.

*Width*.—About 2.2 cm.

*Shape*.—Ovate.

*Apex*.—Obtuse.

*Base*.—Cordate.

*Margin*.—Serrate.

*Texture, upper surface*.—Smooth, glabrous.

*Texture, lower surface*.—Pubescent.

*Venation pattern*.—Pinnate.

*Color*.—Developing and fully expanded leaves, upper surface: Close to 137B; venation, close to 137B. Developing and fully expanded leaves, lower surface: Close to 138B; venation, close to 138B.

*Petiole*.—Length: About 1.7 mm. Diameter: About 2.7 mm. Texture, upper and lower surfaces: Smooth, glabrous. Color, upper and lower surfaces: Close to 144B.

Flower description:

*Flower arrangement and habit*.—Large single flowers arranged on terminal racemes; flowers zygomorphic with five lobes fused at the base and spurred; freely flowering habit with about 21 flowers per raceme; flowers face outwardly.

*Fragrance*.—None detected.

*Flowering response and natural flowering season*.—Early flowering habit, plants begin flowering about three weeks after planting; plants flower freely and continuously from the spring into the fall in Japan.

*Flower longevity*.—Flowers last about five days on the plant; flowers not persistent.

*Inflorescence height*.—About 7.2 cm.

*Inflorescence diameter*.—About 3.4 cm.

*Flower diameter*.—About 1.6 cm by 1.7 cm.

*Flower depth*.—About 4.8 mm.

*Flower buds*.—Length: About 4 mm. Diameter: About 4.7 mm. Shape: Spherical. Color: Close to 62B.

*Corolla*.—Arrangement: Corolla consists of five petals modified into two upright banner petals, two lateral petals and a larger lower lip petal. Banner lobe length: About 5.4 mm. Banner lobe width: About 6.9 mm. Lateral lobe length: About 5.9 mm. Lateral lobe width: About 6.9 mm. Lower lobe length: About 9 mm. Lower lobe width: About 1 cm. Banner and lateral lobes shape: Orbicular. Lower lobe shape: Transversely broadly elliptical. Banner, lateral and lower lobes apex: Rounded. Banner, lateral and lower lobes margin: Entire. Banner, lateral and lower petals texture, upper and lower surfaces: Smooth, glabrous. Spur length: About 5 mm. Spur diameter: About 2 mm. Spur orientation: Positioned towards the flower or pointed inwardly. Color, banner, lateral and lower petals: When opening and fully opened, upper surface: Lighter than 51B; towards the base of the basal petal, close to 6B; color becoming closer to 64D with development. When opening and fully opened, lower surface: Lighter than 54B; towards the base of the basal petal, close to 6B. Spur: Close to 64B.

*Sepals*.—Appearance: Five sepals fused into a star-shaped calyx. Length: About 2 mm. Width: About 1.1 mm. Shape: Lanceolate. Apex: Acute. Margin: Entire. Texture, upper and lower surfaces: Smooth, glabrous.

Color, immature and mature, upper surface: Close to 144B. Color, immature and mature, lower surface: Close to 138B.

*Peduncles*.—Length: About 1.8 cm. Diameter: About 1.2 mm. Angle: Mostly erect. Texture: Pubescent. Color: Close to 144A.

*Pedicels*.—Length: About 1.25 cm. Diameter: About 0.3 mm. Angle: About 45° from the peduncle axis. Texture: Smooth, glabrous. Color: Close to 144B tinted with close to 70C.

*Reproductive organs*.—Androecium: Stamen number per flower: About four. Stamen length: About 2 mm. Anther shape: Bi-lobed, elliptic. Anther length: About 1 mm. Anther color: Close to 7A. Amount of pollen: Scarce. Pollen color: Close to 4A. Gynoecium: Pistil number per flower: One. Pistil length: About 2.4 mm. Style length: About 1.1 mm. Stigma shape: Orbicular. Stigma color: Close to 145C. Ovary color: Close to 144C.

*Seeds and fruits*.—Seed and fruit production have not been observed on plants of the new *Diascia*.

Garden performance: Plants of the new *Diascia* have been observed to have good garden performance and to tolerate wind, rain and temperatures ranging from about 5° C. to about 35° C.

Pathogen & pest resistance: Plants of the new *Diascia* have not been observed to be resistant to pests and pathogens common to *Diascia* plants.

It is claimed:

1. A new and distinct *Diascia* plant named 'Sunjodiropi' as illustrated and described.

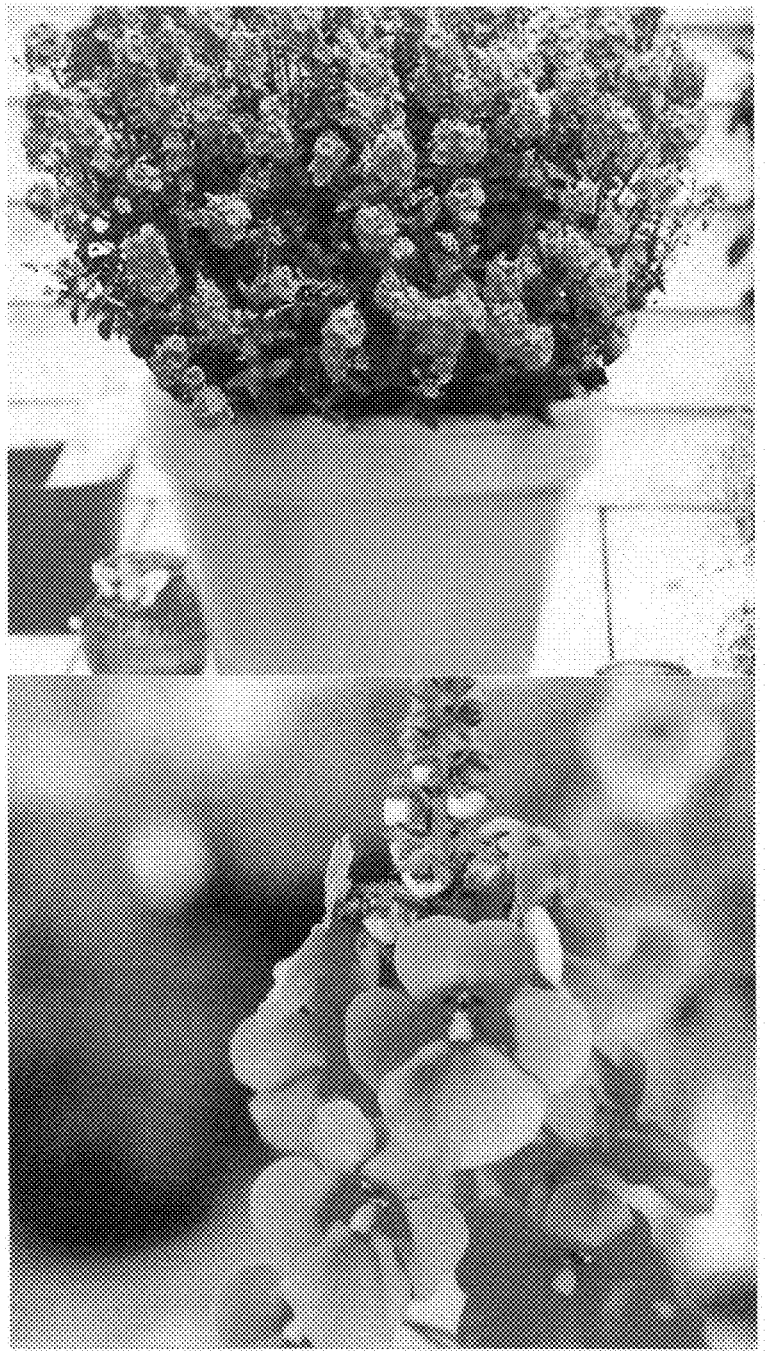

* * * * *